United States Patent
Ma et al.

(10) Patent No.: US 9,897,540 B2
(45) Date of Patent: Feb. 20, 2018

(54) APPARATUS AND METHOD FOR INSPECTING MATERIAL OF AN OBJECT

(71) Applicants: Fu Tai Hua Industry (Shenzhen) Co., Ltd., Shenzhen (CN); HON HAI PRECISION INDUSTRY CO., LTD., New Taipei (TW)

(72) Inventors: Chao-Hung Ma, New Taipei (TW); Shen-Kang Li, Shenzhen (CN); Ning Duan, Shenzhen (CN); Zhi-Ling Chen, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 19 days.

(21) Appl. No.: 15/000,842

(22) Filed: Jan. 19, 2016

(65) Prior Publication Data

US 2017/0191931 A1    Jul. 6, 2017

(30) Foreign Application Priority Data

Dec. 31, 2015   (CN) .......................... 2015 1 1032083

(51) Int. Cl.
| | |
|---|---|
| G01N 21/55 | (2014.01) |
| G01J 1/18 | (2006.01) |
| G01J 1/10 | (2006.01) |

(52) U.S. Cl.
CPC ................ *G01N 21/55* (2013.01); *G01J 1/10* (2013.01); *G01J 1/18* (2013.01)

(58) Field of Classification Search
CPC .... G01N 21/55; G01N 21/57; G01N 21/8422; G01N 21/86; G01N 21/87; G01N 2021/555; G01N 2021/556; G01N 2021/557; G01N 2021/558; G01N 2021/559; G01N 2021/575; G01N 2021/8427; G01N 2021/8433; G01N 2021/8438; G01N 2021/8444; G01N 2021/845; G01N 2021/8472; G01N 2021/8477; G01N 2021/8663; G01N 2021/869; G01J 1/10; G01J 1/12; G01J 1/14; G01J 1/17; G01J 1/18
See application file for complete search history.

(56) References Cited

U.S. PATENT DOCUMENTS

| | | | | |
|---|---|---|---|---|
| 1,961,913 A | * | 6/1934 | Reynolds | G01N 21/474 |
| | | | | 356/408 |
| 2,127,477 A | * | 8/1938 | Carpenter | G01N 21/57 |
| | | | | 250/222.1 |
| 2,546,450 A | * | 3/1951 | Hunter | G01N 21/57 |
| | | | | 250/208.4 |
| 2,565,151 A | * | 8/1951 | Taylor | G01N 21/55 |
| | | | | 250/222.1 |

(Continued)

*Primary Examiner* — Gordon J Stock, Jr.
(74) *Attorney, Agent, or Firm* — ScienBiziP, P.C.

(57) ABSTRACT

A material inspection apparatus includes a light source, a light receiver, a light converter, and a processing unit. The light source is configured to emit light to a surface of an object to be inspected. The light receiver is configured to receive light reflected from the surface of the object. The light converter is configured to convert the light received by the light receiver into an electric current. The processing unit is configured to determine, according to the electric current, a material of the surface of the object.

6 Claims, 2 Drawing Sheets

(56) References Cited

U.S. PATENT DOCUMENTS

| | | | | |
|---|---|---|---|---|
| 3,397,609 A | * | 8/1968 | Kulig | G01B 11/0625 |
| | | | | 250/223 R |
| 3,483,385 A | * | 12/1969 | Heaslip | G01N 21/55 |
| | | | | 250/202 |
| 3,549,264 A | * | 12/1970 | Christie | G01N 21/57 |
| | | | | 250/227.29 |
| 4,189,335 A | * | 2/1980 | Evans | G01B 11/0616 |
| | | | | 156/64 |
| 2005/0211902 A1 | * | 9/2005 | Barry | G01N 21/55 |
| | | | | 250/341.1 |
| 2009/0073421 A1 | * | 3/2009 | Jung | G01J 1/0411 |
| | | | | 356/73 |

* cited by examiner

APPARATUS AND METHOD FOR INSPECTING MATERIAL OF AN OBJECT

FIELD

The subject matter herein generally relates to an apparatus for determining a material of a surface of an object and a method thereof.

BACKGROUND

Generally, power supplies are used for supplying electric power to electronic devices such as computers or servers.

BRIEF DESCRIPTION OF THE DRAWINGS

Implementations of the present technology will now be described, by way of example only, with reference to the attached figures.

DETAILED DESCRIPTION

Figure 1:
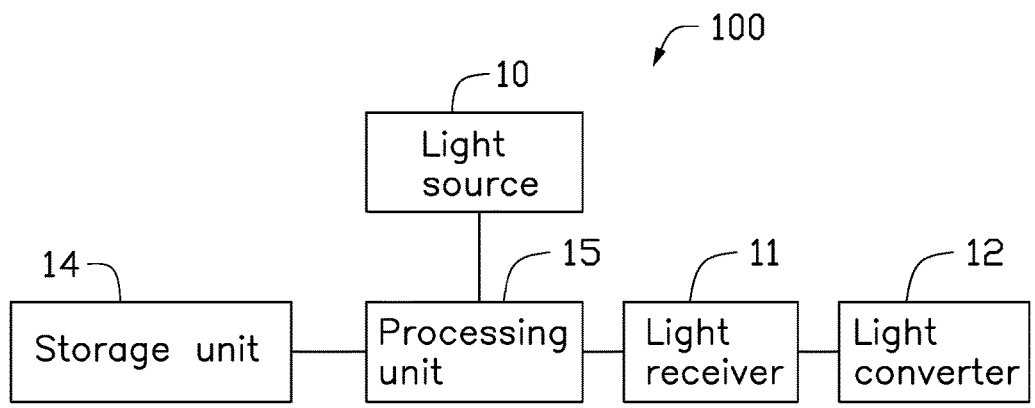
FIG. 1 is a block diagram of an embodiment of a material inspection apparatus.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

The term "comprising" means "including, but not necessarily limited to"; it specifically indicates open-ended inclusion or membership in a so-described combination, group, series and the like.

FIG. 1 illustrates an embodiment of a material inspection apparatus 100. The material inspection apparatus 100 can include a light source 10, a light receiver 11, a light converter 12, a storage unit 14, and a processing unit 15. The light source 10 can emit light at a predetermined angle to a surface of an object to be inspected. In at least one embodiment, the predetermined angle can be between zero and eighty degrees. The light receiver 11 can receive light reflected from the surface of the object. The light converter 12 can convert the light received by the light receiver 11 into an electric current.

The storage unit 14 can store a reference table listing a plurality of light intensities of the light emitted by the light source 10, a corresponding plurality of electric currents, and a corresponding plurality of materials. Each of the plurality of electric currents corresponds to a corresponding light intensity of the light emitted by the light source 10 at the predetermined angle. The processing unit 15 can determine the material of the surface of the object according to the electric current corresponding to the light received by the light receiver 11. The storage unit 14 can be a permanent storage unit of the material inspection apparatus 100 or be a removable storage unit, such as a removable media card, a universal serial bus drive, or other storage device. The processing unit 15 can be a central processing unit, a microprocessor, or other data processing chip.

In at least one embodiment, the processing unit 15 can display a result according to the reference table. The result can be the material of the surface of the object. In at least one embodiment, the result is displayed on a display device (not shown).

Figure 2:
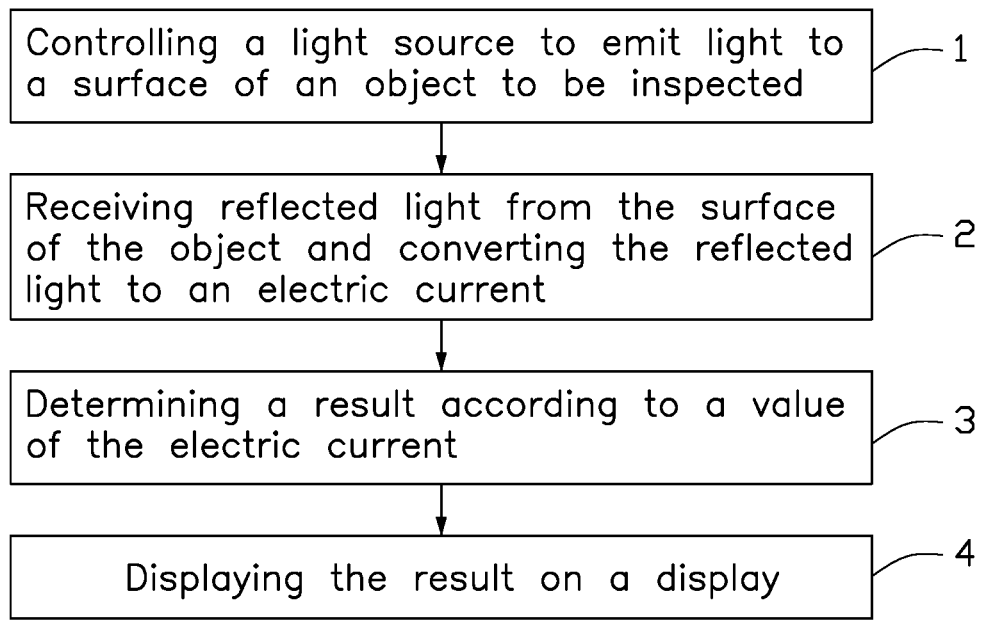
FIG. 2 is a flowchart of an embodiment of a method for inspecting a surface of an object.

FIG. 2 illustrates a flowchart of an exemplary method for inspecting a surface of an object. The example method is provided by way of example, as there are a variety of ways to carry out the method. The method described below can be carried out using the configurations illustrated in FIG. 1, for example, and various elements of the figure are referenced in explaining the example method. Each block shown in FIG. 2 represents one or more processes, methods, or subroutines carried out in the example method. Furthermore, the illustrated order of blocks is by example only, and the order of the blocks can be changed. Additional blocks can be added or fewer blocks can be utilized, without departing from this disclosure. The example method can begin at block 1.

At block 1, a processing device can control a light source to emit light to a surface of an object to be inspected. In at least one embodiment, the light source can emit light at a predetermined angle to the surface of an object to be inspected. In at least one embodiment, the predetermined angle can be between zero and eighty degrees.

At block 2, a light receiver can receive reflected light from the surface of the object, and a light converter can convert the light received by the light receiver into an electric current.

At block 3, the processing unit can determine a result according to a value of the electric current. The result can be a material of the surface of the object. A storage unit can store a reference table listing a plurality of light intensities of the light emitted by the light source, a corresponding plurality of electric currents, and a corresponding plurality of materials. Each of the plurality of electric currents corresponds to a corresponding light intensity of the light emitted by the light source at the predetermined angle. The processing unit can determine the material of the surface of the object according to the electric current corresponding to the light received by the light receiver.

At block 4, the processing unit can display the result on a display.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. An apparatus for inspecting material of an object comprising:
   a light source configured to emit light to a surface of the object to be inspected;
   a light receiver configured to receive light reflected from the surface of the object;
   a light converter configured to convert the light received by the light receiver into an electric current;

a processor coupled to the light source; and a non-transitory storage unit coupled to the processor and the processor configured to: determine, according to the electric current and a reference table, the material of the surface of the object, wherein the storage unit stores the reference table listing a plurality of light intensities of the light emitted by the light source, a corresponding plurality of materials, and a corresponding plurality of electric currents, the plurality of light intensities and the corresponding plurality of electric currents correspond to the light emitted by the light source at a predetermined angle.

2. The apparatus for inspecting material of an object as in claim 1, wherein the processor determines the material of the surface of the object according to the electric current converted from light emitted at the predetermined angle by the light source.

3. A method for inspecting material of an object applied in the apparatus for inspecting material of an object of claim 1, the method comprising:

controlling, by the processor, the light source to emit light to the surface of the object to be inspected;

receiving, by the light receiver, light reflected from the surface of the object to be inspected;

converting, by the light converter, the light received by the light receiver into an electric current; and determining, by the processor, the material of the surface of the object according to the reference table, wherein the storage unit stores the reference table listing the plurality of light intensities of the light emitted by the light source, the corresponding plurality of materials, and the corresponding plurality of electric currents, the plurality of light intensities and the corresponding plurality of electric currents correspond to the light emitted by the light source at the predetermined angle.

4. The apparatus for inspecting material of an object as in claim 2, wherein the processor controls the light source to emit light at the predetermined angle.

5. The method for inspecting material of an object as in claim 3 comprising displaying, by the processor, a result, the result being the material of the surface of the object.

6. The method for inspecting material of an object as in claim 3, wherein the light source emits the light at the predetermined angle and at a predetermined intensity to the surface of the object.

* * * * *